United States Patent [19]

Arnold

[11] Patent Number: 5,252,121
[45] Date of Patent: Oct. 12, 1993

[54] AMALGAM-GLASS IONOMER BONDING SYSTEM

[75] Inventor: Thomas J. Arnold, Winslow, Ind.

[73] Assignee: Mion International Corporation, Winslow, Ind.

[21] Appl. No.: 872,501

[22] Filed: Apr. 23, 1992

Related U.S. Application Data

[63] Continuation-in-part of Ser. No. 748,679, Aug. 22, 1991, abandoned.

[51] Int. Cl.$^5$ ............................ C09K 3/00; A61C 5/00
[52] U.S. Cl. ................................... 106/35; 433/228.1
[58] Field of Search ............... 106/35; 420/504, 527; 433/228.1

[56] References Cited

U.S. PATENT DOCUMENTS

| | | | |
|---|---|---|---|
| 3,676,112 | 7/1972 | Muhler | 420/504 |
| 3,933,961 | 1/1976 | Burns | 264/111 |
| 4,064,629 | 12/1977 | Stoner et al. | 32/15 |
| 4,654,007 | 3/1987 | Sigler et al. | 433/236 |
| 4,684,347 | 8/1987 | Palaghias | 433/228.1 |
| 4,738,722 | 4/1988 | Ibsen et al. | 106/35 |
| 4,813,871 | 3/1989 | Friedman | 433/90 |
| 4,872,936 | 10/1989 | Engelbrecht | 156/307.3 |

OTHER PUBLICATIONS

Ionosphere product instructions, Goldsmith & Revere, Englewood, N.J.
Sybraloy product instructions, Kerr Manufacturing Company, Romulus, Mich.
Luxalloy product instructions, Degussa AG, Frankfort, West Germany.
KETAC-CEM Radiopaque product instructions, ESPE Premier Sales Corp., Norristown, Pa.
Durelon product instructions, Premier Dental Products Co., Norristown, Pa.
Veratex product instructions, Veratex Corporation, Troy, Mich., Jan. 1980.
Hotz et al., The Bonding of Glass Ionomer Cements to Metal and Tooth Substrates, British Dental Journal, Jan. 1977; 142:41–47.
Matis et al., How Finishing Affects Glass Ionomers, The Journal of the Am. Dental Assoc., Jul. 1991; 122:43–46.
Scherer, Reinforced Glass Ionomer Cement vs. Zinc Phosphate Cement, 18th Session of the American Assoc. for Dental Research, San Francisco, Calif.
Johnson et al., Dentin Bonding Systems: A Review of Current Products and Techniques, The Journal of the Am. Dental Assoc., Jul. 1991; 122:34–41.
Jablonski, Illustrated Dictionary of Dentistry, W. R. Saunders Co., Philadelphia, Pa., pp. 10, 33–35, 37–38, 879–880.
Cardosa et al., Low-Silver amalgam restorations; A two-year clinical evaluation, Dental Materials, Jul. 1989; 5:277–80.
Osborn, Clinical Assessment of 14 Amalgam Alloys, General Dentistry, May–Jun. 1990:206–208.
Powell et al., Effect of Admixed Indium on Mercury Vapor Release from Dental Amalgam, Journal of Dental Research, Aug. 1989; 68(8):1231–1233.
Aboush et al., The bonding of glass ionomer cements to dental amalgam, British Dental Journal, 1989; 166:255–257.
Mojon et al., Maximum Bond Strengths of Dental Luting Cement to Amalgam Alloy, Journal of Dental Research, Nov. 1989; 68(11):1545–1549.
Mecurial Debate, Science; d55(13):1356–1357, Mar. 13 1992.
Fasbinder et al., Tensile Bond Strength of Dental Adhesives to Dentin and Enamel, Dental Materials, Jul. 1989; 5:272–276.

(List continued on next page.)

*Primary Examiner*—Mark L. Bell
*Assistant Examiner*—Margaret Einsmann
*Attorney, Agent, or Firm*—Baker & Daniels

[57] ABSTRACT

Metal bases, metal salts and/or metal oxides are added to an amalgam restoration formula for use in conjunction with a glass ionomer cement to restore a tooth lesion. The additive is comprised of an amount of metal bases, metal salts and/or metal oxides, such as the powder of a polycarboxylate dental cement, sufficient to improve the bond strength between wet glass ionomer cement applied to the tooth lesion and the wet improved amalgam applied to the wet cement. As a result, the retentive quality of such a restoration is improved and therefore may permit a lesion to be filled with amalgam rather than requiring extraction or the application of a prosthesis.

13 Claims, No Drawings

OTHER PUBLICATIONS

Gilmore et al., Operative Dentistry, C. V. Mosby Company; 1973, pp. 196-200, 279-281.

New Era of Composite Bonding, Dentistry Today, Jun./Jul. 1991, pp. 32, 34.

New Products—Adhesive System, Dental Products Report, Sep. 1991.

Shofu Advertisement, Dental Products Report, Sep. 1991, p. 65.

Dentistry Techniques, Dental Products Report, Sep. 1991, pp. 74-75.

Retentive Pins . . . Are they everything they're cracked up to be?, Advertisement, American Dental Assoc. News, 1991; 22, 14: p. 15.

Amalgambond—The first bonding agent for amalgam, Advertisement, American Dental Assoc. News, 1991; 22,13; p. 28.

Starting today, you may never have to re-cement again . . . ever. Advertisement, Dentistry Today, 1991; 10,6: p. 17.

Geristore: A Pediatric/Geriatric Restorative, video tape by Dr. Ronald Jordan, American Society for Clinical Research, No. 1006780, V1.0.

Illustrated Dictionary of Dentistry, W. B. Saunders Company, pp. 37-38.

Aboush et al., An evaluation of the bonding of glass-ionomer restorations to dentine and amalgam, British Dental Journal, 1986; 16 179-184.

Staninec et al., *Bonding of Amalgram to tooth structure:* Tensile adhesion and microleakage tests; Journal of Prosthetic Dentistry; 59:4, Apr. 1988, pp. 397-402.

Rueggeberg et al., *Bond Strength of Panavia EX to Dental Amalgam;* International Journal of Prosthodontics; 2:4; pp. 371-375.

3. Torii et al., *Inhibition in Vitro of Caries around amalgam Restorations by Bonding Amalgam to Tooth Structure;* Operative Dentistry; 14; 1989; pp. 142-148.

Shimizu et al., *Bond Strength between Amalgam and Tooth Hard Tissues with Application of Flouride, Glass Ionomer Cement and . . . ,* Dental Materials Journal; 52; 1986; pp. 225-232.

Varga et al., *Bonding of Amalgam Filling to Tooth Cavity with Adhesive Resin;* Dental Materials Journal; 5:2; 1986; pp. 158-164.

Lacy et al., *The bonded amalgam restoration;* Quintessence International; 20:7; 1989, pp. 521-524.

Cooley et al., *Bond strength of resin to amalgam as affected by surface finish; Quintessence International; 20:4; pp. 237-239, 1989.*

Hibler et al.; *Bond Strength Comparisons of Repaired dental Amalgams;* Quintessence International; 19:6; 1989; pp. 411-415.

Yu et al., *Experimental use of a bonding agent to reduce marginal microleakage in amalgam restorations;* Quintessence International; 18:11; 1987; pp. 783,787.

Colon et al., *Les amalgames colles: technique direct et indirecte;* Revue D'Odonto Stomatologie; 16:1; 1987; pp. 9-18.

Warren et al., *Bonding amalgam to glass ionomer with PAA;* Dental Materials; 4; 1988; pp. 191-196.

Stevenson, *Modified Bonded Amalgam Technique* (letter to the editor); British Dental Journal; Dec. 24, 1983; p. 401.

*The Government Chemist Plays Host;* British Dental Journal; Apr. 23, 1983; p. 268.

Braden, *The Effect of Technology on Clinical Practice,* Jul. 1 to 3, 1983.

*Effects of Polycarboxylate and Glass-Ionomer cements on Stainless Steel crown Retention;* British Dental Journal; p. 218, 1983.

Pearson, *Finishing of Glass-Ionomer Cements;* British Dental Journal; 155; 1983; pp. 226-228.

*Opacity of Glass-Ionomer Cements,* Acta Oclontol Scand. 41:155-157, 1983.

Prodger et al., *ASPA Adhesion Study;* British Dental Journal; 143, 1977; pp. 266-274.

*Dentist's Desk Reference:* Materials, Instruments and Equipment, American Dental Association; 1981, pp. Preface & 84-54.

Expansion of the Acceptance Program for dental materials and devices; glass ionomer cements; JADA, 99; Aug. 1979; pp. 227-228.

Reported Sensitivity to glass ionomer luting cements; JADA; 109; Sep. 1984; p. 476.

Status report on the glass ionomer cements; JADA; 99; Aug. 1979; pp. 221-224.

Dentist's Desk Reference; *Materials, Instruments and equipment;* American Dental association; 1983; pp. Preface & 118-119.

Mercurial Debata, Science; d55(13):1356-1357, 1992.

Curtis, *The Use of Dental Amalgam–An Art or a Science?,* 1992 Jul./Aug. Dental Update pp. 239-245.

Watson, *The interfacial region of the tooth/glass ionomer restoration: A Confocal optical microscope study,* Am J Dent 1991; 4: 303-310.

AMALGAM-GLASS IONOMER BONDING SYSTEM

CROSS REFERENCE TO RELATED APPLICATIONS

This is a continuation-in-part of application Ser. No. 07/748,679 filed Aug. 22, 1991 now abandoned.

FIELD OF THE INVENTION

This invention relates to a system for the restoration of lesions in living teeth, and in particular, to a system for chemically bonding amalgam to dentin.

BACKGROUND OF THE INVENTION

Because conventional amalgam restorations rely purely on mechanical retention to the tooth, they are not suitable in instances when a tooth is severely decayed and has little structure left to which the filling may be attached. Amalgam is created by mixing (amalgamation or trituration) mercury with what is often referred to as amalgam alloy. Amalgam alloy is a powder composed of various alloyed metals and is primarily composed of a silver-tin alloy. When mercury is mixed with the silver-tin alloy, a silvery paste results which is applied for condensation into the prepared lesion or cavity. However, a conventional amalgam restoration in a tooth with even only a moderate amount of decay may fail over time due to recurrent decay, lack of retention, or continued stress breakdown of the remaining tooth structure. Therefore, the patient is often faced with the choice of removing the tooth or the application of a crown.

In some instances, retentive pins are used to affix restorations to a tooth. However, retentive pins are an added expense, take time to clinically place, can weaken the restoration, create stresses within the tooth, and may also result in pulpal exposure. Thus, it is desirable to provide a dental restoration system which does not utilize pins or other similar mechanical mechanism so as to limit the stress placed on the tooth.

Many types of materials have been used to affix a restoration to a tooth, including glass ionomer cement and dentin bonding systems. Glass ionomer cement bonds to tooth structure dentin and has been used for restorative materials, cavity liners, bases, and crown cements. Glass ionomer cements are prepared for use, for example, by mixing a powder comprised of calcium aluminum silicate glass and a liquid comprising an aqueous solution of polyacrylic acid. As a crown cement, the glass ionomer cement is mixed, placed into the crown and, before the cement hardens, the crown is placed over the prepared tooth. As the glass ionomer cement hardens, the crown is retained on the tooth, and, after complete hardening of the cement, an excellent bond between the tooth and crown is formed. In other situations, glass ionomer cement may be applied to a tooth and allowed to harden to form a liner or base on which the amalgam may then be applied to restore the tooth using conventional techniques.

Studies have been conducted to determine the capability of glass ionomer cements to adhere to various materials, including the tests disclosed in Hotz, et al., *The Bonding of Glass Ionomer Cements to Metal and Tooth Substrates*, British Dental Journal, 1977; 142: 41–47. This study demonstrated that glass ionomer cement bonds well with dentin and enamel, and also adheres to some cast solid metals. Adherence to a cast solid metal is most successful when the surface of the metal is first etched with an acid, such as citric acid, before applying the glass ionomer cement. Improved adherence to etched metal indicates that adherence is primarily attributable to a mechanical, as opposed to a chemical, bond.

Results of studies such as Hotz et al., have provided a basis for the use of glass ionomer cements in various dental procedures. For example, in U.S. Pat. No. 4,654,007, a layer of glass ionomer cement is applied to a tooth before attaching a porcelain restoration. After proper hardening of the cement, the cement is etched with an acid to create microscopic surface irregularities which facilitate mechanical retention of the porcelain restoration to the tooth. The method disclosed in U.S. Pat. No. 4,738,722 is similar in that the glass ionomer cement disclosed is hardened and etched with an acid before the restoration material is placed into the cavity preparation. This method protects the pulp of the tooth by providing a layer of glass ionomer cement above the pulp.

The current restoration methods using glass ionomer cements have proven to be successful in restoring significant lesions. For example, Matis, et al., *How Finishing Affects Glass Ionomers*, 1991; 122: 43–46, describes a five year study to determine the effectiveness of restorations involving the use of glass ionomer cements and concluded that the glass ionomer cements are outstanding in their retentive capability. Also, researchers continue to improve the retention capability of the cements. For example, the polymerizable cement mixtures disclosed in U.S. Pat. No. 4,872,936 demonstrate increased mechanical strength, lower solubility, and exhibit no outstanding separation phenomena.

However, one shortcoming of using glass ionomer cements in present restorative techniques is the glass ionomer cement must be allowed to harden before it is etched with acid. This results in an undesirable time delay and increases the risk that damage to the tooth's nerve might occur while etching the hardened glass ionomer. Therefore, it is desirable to develop a dental restoration system which is efficient and requires relatively little time to perform.

In instances when hardened glass ionomer has been used as a base for amalgam, studies show that the glass ionomer shrinks, leaving a slight 60–80 um gap between the hardened glass ionomer and the hardened amalgam. Scherer, *Reinforced Glass Ionomer Cement vs. Zinc Phosphate Cement*, 18th Annual Session of the American Association for Dental Research, San Francisco, Calif. Thus, the hardened glass ionomer does not adequately bond the amalgam to the tooth.

Dentin bonding systems which utilize cements other than glass ionomer cements, such as those discussed in Johnson, et al., *Dentin Bonding Systems: A Review of Current Products and Techniques*, The Journal of the American Dental Association, 1991; 122: 34–41, have recently become available. The cements used in these dentin bonding systems are applied to the tooth prior to filling the tooth or to the application of a restoration. However, before being applied to the tooth, the tooth is etched with an acid to create irregularities to which the dentin bonding systems are micromechanically bonded. These systems have not been well-received due to the risk of pain and damage if the acid contacts sensitive dental nerves. In fact, Johnson et al. identifies several cautions in the use of dentin bond systems and suggests the use of a protective liner for deep lesions. Therefore, it is desirable to develop a dental restoration system which does not require etching of the tooth or of the cement.

It is also known to prepare a tooth cavity with enhanced glass ionomer cement material in which metal alloy particles are added to the glass ionomer cement. Such materials are used as a base or liner under restorations. The additive metal alloy particles may be of the same composition as is used in the powder component of a dental amalgam, that is to say, an amalgam alloy is used. However, these materials have a tendency over time to discolor the dentin and can provide an unsightly aesthetic appearance.

The invention disclosed in U.S. patent application Ser. No. 07/748,679, filed Aug. 22, 1991, now abandoned, the disclosure of which is incorporated herein by reference, comprises a dental restoration system that works well with conventional materials, specifically glass ionomer cement and amalgam, to allow the tooth to be filled instead of being extracted or requiring the application of a prosthesis such as a crown or bridge. Such a system is inexpensive to use and results in an improved bond strength over prior methods.

It is desirable to develop an amalgam-glass ionomer bonding system with an increased bond strength to ensure that such a restoration will remain intact for an extended period of time.

OBJECTS OF THE INVENTION

Accordingly, it is one object of the present invention to provide an amalgam-glass ionomer bonding system with improved bond strengths.

It is another object of the present invention to provide a dental restoration method which is reliable, inexpensive and expedient.

It is another object of the present invention to provide a dental restoration system that does not require pins or acid etching.

It is another object of the present invention to provide a dental restoration system which bonds to dentin, seals dentin tubules and eliminates the need for unnecessary extraction.

It is another object of the invention to provide a dental restoration system that internally bonds the remaining crown of a tooth together so as to avoid continued cracking of the tooth enamel.

It is another object of the present invention to provide a dental restoration system which is able to strongly hold large amalgam fillings.

It is another object of the present invention to provide an amalgam filling with an increased life expectancy.

SUMMARY OF THE INVENTION

Metal bases, metal salts and/or metal oxides are added to an amalgam restoration formula for use in conjunction with a glass ionomer cement to restore a tooth lesion. The additive is comprised of an amount of metal bases, metal salts and/or metal oxides, such as the powder of a polycarboxylate dental cement, sufficient to improve the bond strength between wet glass ionomer cement applied to the tooth lesion and the wet improved amalgam applied to the wet cement. As a result, the retentive quality of such a restoration is improved and therefore may permit a lesion to be filled with amalgam rather than requiring extraction or the application of a prosthesis.

DETAILED DESCRIPTION

U.S. patent application Ser. No. 07/748,679 now abandoned, filed Aug. 22, 1991, discloses a method and composition for restoring a tooth using amalgam and glass ionomer cement. Specifically, a tooth lesion is first prepared to receive an amalgam filling using conventional techniques. If sufficient tooth structure is present, the tooth may be undercut to provide improved mechanical retention for the completed filling. Liquid, or wet, glass ionomer cement is then applied to the prepared tooth lesion. The glass ionomer cement used in this invention preferably has a set time of 5-10 minutes and contains fluoride ions to assist in preventing tooth decay by releasing fluoride ions into the dentin over time. Such glass ionomer cements are available from a variety of sources including the GlasIonomer Cement, Type I distributed by Shofu Dental Corporations of Menlo Park, Calif. While the glass ionomer cement layer is still wet, a layer of wet amalgam, such as Valiant Phd, is placed on the glass ionomer layer using conventional amalgam application techniques. The glass ionomer and amalgam layers are allowed to harden to form a solid laminate structure that sufficiently restores the tooth. This method and composition results in a remarkably strong bond between the glass ionomer cement and the amalgam after the amalgam has hardened.

Conventional amalgam of the type commonly used in dentistry is comprised of two components: amalgam powder comprised of various alloyed metals, and mercury. Generally, the amalgam powder, commonly referred to as "amalgam alloy," is comprised of a silver-tin alloy, with trace amounts of copper with or without zinc. When amalgam powder is mixed (also referred to as trituration or amalgamation) with mercury, the substance known as amalgam results. The present invention includes a composition for amalgam which strengthens the bond of a restoration to a tooth where that restoration has been created through the application of wet amalgam onto wet glass ionomer cement. Specifically, in one embodiment, a source of alloy-forming compounds, such as metal salts, metal bases and metal oxides, is added to the amalgam powder prior to amalgamation and application of the amalgam in the above-identified dental procedure. Metal bases, metal salts and metal oxides include, for example, phosphates, nitrates, sulfates, carbonates, oxides, hydroxides and halogens of the particular alloy-forming metal utilized. Materials of this type which have been used in dentistry for other purposes with some prevalence and considered most likely candidates as additives include zinc phosphate, zinc oxide, magnesium sulfate, stannous fluoride and silver nitrate. Other additives are contemplated for use herein, but must be scrutinized according to the effect such additives may have in the patient. For example, iodine has adverse affects in many patients whereas tin oxide does not affect the patient.

One readily available source of metal bases, metal salts, and metal oxides is the powder component of a polycarboxylate cement. Polycarboxylate cements are created by mixing a powder component, usually containing zinc oxide and magnesium sulfate and, often, stannous fluoride, with a liquid comprising an aqueous solution of polyacrylic acid. The constituents of the polycarboxylate cement powder are not alloyed as are the constituents of an amalgam powder. In the present invention, only the powder component of the polycarboxylate cement is used as an additive. Favorable results have been obtained using the powder component of Durelon ® polycarboxylate cement manufactured in West Germany and distributed by Premier Dental Products Company of Norristown, Pa., and Veratex, a zinc polycarboxylate cement distributed by Veratex Corporation of Troy, Mich.

In one embodiment of the present invention, small quantities of the powder component of the polycarboxylate cement are added to the amalgam powder prior to the addition of mercury to the amalgam powder and to the trituration of the mixture to thereby result in an improved amalgam. As used herein and in the claims, "improved amalgam powder" means a dental amalgam powder or silver-tin alloy to which a constituent comprising metal bases, metal salts and/or metal oxides has been added. Also, as used herein and in the claims, "improved amalgam" means an improved amalgam powder mixed with mercury.

Pull strength tests using the improved amalgam of the present invention were performed using KETAC ®-CEM Radiopaque glass ionomer cement distributed by ESPE Premier Sales Corp. of Norristown, Pa. and an improved amalgam comprising Sybraloy amalgam, available from Kerr Manufacturing Company of Romulus, Mich., and Durelon ® polycarboxylate cement powder. In these tests, the improved amalgam powder was created by mixing 11 milligrams of the powder component of the Durelon ® polycarboxylate cement with 400 milligrams of amalgam powder. The improved amalgam powder was then triturated with 400 milligrams of mercury in the usual manner, thereby forming the improved amalgam. In the samples tested, the additive comprised about 2.7% by weight of the powder mixture, or 1.4% by weight of the improved amalgam. Several plugs of equal size, shape and proportion were formed using the improved amalgam and the glass ionomer cement. Specifically, a sandwich of wet improved amalgam, wet glass ionomer cement, and wet improved amalgam was formed in plastic molds, the plastic of which does not adhere to amalgam or to glass ionomer cement. These plugs were then allowed to dry for 24 hours. One end of the plug, comprising hardened improved amalgam, was clamped to a fixed table surface, and the other end, also comprising hardened improved amalgam was attached to a scale. Weights were then added to the scale until the plug broke apart at the interface between the hardened glass ionomer cement and the hardened amalgam. Comparative plugs were also formed using conventional amalgam, i.e., amalgam to which no additives were made, and glass ionomer cement. These comparative plugs were tested for pull strength as described above to provide as baseline upon which to compare the bond strength of the improved amalgam to conventional amalgam.

The comparative plugs exhibited a bond strength of 147 psi, whereas the plugs formed from the improved amalgam exhibited a bond strength of 187 psi. It will be appreciated by those of skill in the art that bond strengths of 187 psi are quite significant and help to ensure that the restoration remains securely in place so as to minimize future restorations of the same lesion.

Durelon ® and Veratex are suitable for use as additives with a variety of commercially available amalgams, such as Ionosphere distributed by Goldsmith & Revere of Englewood, N.J., and Luxalloy ® manufactured by Dequssa AG of Frankfort, West Germany, and similar improvements in bond strengths may be obtained.

Various amalgam additives may be used to enhance the bond between the glass ionomer cement and the improved amalgam. These include metal bases, metal salts and metal oxides. It is believed that the additives improve the bonding reactions as they produce carboxylate ion groups upon contact with the polyacrylic acid of the wet glass ionomer cement. It is further believed that the carboxylate ions of the glass ionomer cement then ionically bond to the available cations of the amalgam. The glass ionomer cement's polyacrylic acid groups form metal carboxylate salts with the metal cations of the improved amalgam. This "neutralization" of the carboxylic acid improves wetting of the surface of the improved amalgam through its interaction with the polyacrylic acid component of the glass ionomer cement, and further ionic bonding is created by the metal carboxylate salts forming at the reacted surfaces. These results, which are strong bonds forming at the surface of the amalgam, increase the strength of the resulted union between the cement and amalgam.

It is interesting to note that the improved amalgam powder containing the conventional amalgam powder and the additive of polycarboxylate cement powder, when mixed with the prescribed amount of mercury for the amalgam powder results in a "wetter" mixture than when no additive is present. Therefore, as will be appreciated by those of skill in the art, it is possible that the amount of mercury required for use with the improved amalgam powder to create improved amalgam could be reduced to obtain handling characteristics like those of conventional amalgam. By reducing the content of toxic mercury in the improved amalgam, the risk to the patient is thereby reduced.

It is believed that the amount of additive required to result in an improved amalgam according to the present invention ranges from a trace, 0.001%, to 25% of the total weight of the improved amalgam. Actual percentages by weight of additives in the improved amalgam may vary according to the weight of the compounds containing metal bases, metal salts or metal oxides added, and is limited only by the distortion of the amalgam in the presence of excessive additive. Preferably, the additive comprises about 1-5% by weight of the improved amalgam powder.

It will be appreciated by those of skill in the art that the restoration of major tooth lesions according to the present invention can be accomplished in instances where more expensive crowns or bridges would ordinarily be required. In addition, the procedure of the present invention can be accomplished in much less time. Moreover, due to the strong bond of the amalgam to the glass ionomer cement, the restoration will last longer than conventional amalgam fillings, even for large lesions. Also, the use of glass ionomer cement seals dentin tubules, which helps eliminates post restorative sensitivity. Finally, since the glass ionomer cement may contain fluoride, it provides a fluoride release which assists in inhibiting recurrent decay.

The amalgam restorative formula which is improved as described herein should be considered as a restorative material termed an improved amalgam. It will be appreciated by those of skill in the art that other amalgam bonding systems or methods utilizing materials other than those disclosed herein will find the improved amalgam to be compatible with the particular system or material (such as acrylic bonding agents) used. Also, as noted herein, an improved amalgam is "wetter" than a conventional amalgam. This implies that the amount of mercury required for use of the improved amalgam in accordance with the restoration method disclosed in U.S. patent application Ser. No. 07/748,679, filed Aug. 22, 1991, or the use of any amalgam, conventional or improved, utilized for any other purpose, may be reduced. Hence, the use of the improved amalgam for any dental procedure is anticipated and is expected by this invention.

I claim:

1. A method of restoring lesions in a living tooth, comprising the steps of:
   applying a wet glass ionomer cement to a lesion;
   placing a wet improved amalgam restorative material directly on the wet glass ionomer cement, the improved amalgam comprising at least one additive selected from the group consisting of metal bases, metal salts and metal oxides; and
   allowing the wet glass ionomer cement and the wet improved amalgam to harden, thereby bonding the improved amalgam restorative material to the tooth.

2. The method of claim 1, wherein the amalgam restorative material is prepared by the steps of: providing an amalgam alloy; introducing an additive selected from the group consisting of metal salts, metal bases and metal oxides to the amalgam alloy to form an improved amalgam alloy; and, triturating the improved amalgam alloy with mercury to form the amalgam restorative material.

3. The method of claim 1, wherein the amalgam restorative material comprises the combination of amalgam and an additive, additive is present in the amalgam in an amount sufficient to improve the bonding strength between the glass ionomer cement and the improved amalgam restorative material.

4. The method of claim 2, wherein the additive comprises the powder component of polycarboxylate cement.

5. The method of claim 3, wherein the additive comprises at least one of zinc phosphate, zinc oxide, magnesium sulfate, stannous fluoride, silver nitrate and tin oxide.

6. The method of claim 2, wherein the additive is present in the amalgam restorative material in an amount of from about 0.001% to about 25% by weight of the restorative material.

7. The method of claim 2, wherein the additive is present in an amount of from about 1% to about 5% by weight of the amalgam alloy.

8. The method of claim 3, wherein the additive is added in an amount sufficient to form a bond between the glass ionomer cement and the amalgam restorative material having a bond strength of at least 40 psi.

9. The method of claim 3, wherein the additive is added in an amount sufficient to form a bond between the glass ionomer cement and the amalgam restorative material having a bond strength of at least 180 psi.

10. A restoration for restoring lesions in a living tooth, comprising a layer of glass ionomer cement bonded to the tooth; and a layer of amalgam disposed on the layer of glass ionomer cement, the restoration having been formed according to the method of claim 1.

11. The restoration of claim 10, wherein the dental amalgam further comprises an amalgamation of amalgam alloy and mercury, and wherein said additive comprises a sufficient amount to enhance bonding between the glass ionomer cement and the dental amalgam.

12. The restoration of claim 10, wherein the additive comprises a least one of zinc phosphate, zinc oxide, magnesium sulfate, stannous fluoride, silver nitrate and tine oxide, and wherein said additive comprises between about 0.001% and 25% by weight of the dental amalgam.

13. The restoration claim 10, wherein the additive is added in an amount sufficient to form a bond having a bond strength of at least 180 psi between the glass ionomer cement and the dental amalgam when a layer of the wet dental amalgam is applied to a layer of wet glass ionomer cement, and the layers are allowed to harden.

* * * * *